US00PP12655P2

(12) United States Plant Patent
Williams

(10) Patent No.: US PP12,655 P2
(45) Date of Patent: May 28, 2002

(54) ROSE PLANT NAMED 'MAGIC BEAUTY'

(76) Inventor: J. Benjamin Williams, 2800 Elnora St., Silver Spring, MD (US) 20902

( * ) Notice: Subject to any disclaimer, the term of this patent is extended or adjusted under 35 U.S.C. 154(b) by 0 days.

(21) Appl. No.: 09/433,750

(22) Filed: Nov. 4, 1999

(51) Int. Cl.[7] ..... A01H 5/00
(52) U.S. Cl. ..... Plt./132

(58) Field of Search ..... Plt./132, 130, 131

*Primary Examiner*—Bruce R. Campell
*Assistant Examiner*—June Hwu
(74) *Attorney, Agent, or Firm*—Ratner & Prestia

(57) ABSTRACT

A new rose variety of the hybrid tea class having long stems; large, bright purple red buds with yellow reverse; large, bright purple red and yellow blended flowers; and a vigorous, upright habit of growth.

1 Drawing Sheet

FIELD OF THE INVENTION

This invention relates to a new and distinct variety of rose plant of the hybrid tea rose class characterized having beautifully formed buds on strong straight stems. The flower color is a deep purple red on the other edge of the inside of the petal and a clear golden yellow on the reverse of each petal. The plant is a very vigorous upright growing plant with excellent branching.

SUMMARY OF THE INVENTION

The present invention relates to a new and distinct variety of rose plant of the hybrid tea class which was originated by me by crossing the rose variety known as 'Love' (U.S. Plant Pat. No. 4,437) with the variety known as 'Gold Medal' (U.S. Plant Pat. No. 5,177). As a result of this breeding, I have produced a new and improved rose variety which is distinguished from its parents, as well as from all other rose varieties of which I am aware, as evidenced by the following unique combination of characteristics which are outstanding therein:

(1) Exceptionally long straight stems
(2) Excellent bright purple red and golden yellow bicolor flowers
(3) Long flower buds
(4) Large open flower
(5) Vigorous upright habit of growth
(6) Disease-resistant plant and winter hardy Asexual reproduction of this new variety by budding was first performed in West Grove, Chester County, Pa., U.S.A. Asexual reproduction of this new variety in West Grove, Pa., U.S.A., and Litchfield, Ariz. U.S.A., shows that the foregoing and all other characteristics come true to form and are established and transmitted through successful propagation.

BRIEF DESCRIPTION OF THE ILLUSTRATION

The accompanying illustration shows typical specimens of the vegetative growth and flower of this new variety in different stages of development, depicted in color as nearly true as it is reasonably possible to make the same in a color illustration of this character.

DETAILED DESCRIPTION OF THE NEW VARIETY

The following is a detailed description of my new rose cultivar with color descriptions using terminology in accordance with a Royal Horticulture Society Colored Charts (R.H.S.C.C.), except where ordinary dictionary significance of color is indicated.

Parentage: Seedling.
*Seed parent.*—'Love'. (U.S. Plant Pat. No. 4,437).
*Pollen parent.*—'Gold Medal'. (U.S. Plant Pat. No. 5,177).
Class: Hybrid tea.

The following observations are made of four-year old specimens grown outdoors in Chester County, Pa., during the months of June and September.

FLOWER

Blooming habit: Recurring, continuous.

A. Bud:
*Size.*—Large. About 1¾ to 2 inches long when the petals start to unfurl.
*Form.*—Long and pointed.
*Color.*—When the sepals first divide, the outer petals are close to Yellow-Orange Group 19-C with the petal edges and tips close to Red Purple Group 60-A.
*Sepals.*—Medium, tapered, curling back as bud opens extending ⅓×–½ the length of the open bud. Length — about 1¾ to 2 inches. There are three normally appendaged sepals. There are two unappendaged sepals with hairy edges. Shape — triangular, pointed with slight serration at tip. Texture — smooth. Color: Upper side — Green Group 141-C; Underside — Green Group 139-D.
*Peduncle.*—Length — 3½ to 4 inches. Strength — straight, erect, and heavy. Aspect — smooth. Color — Green Group 144-B.

B. Bloom:
*Size.*—Large. Average open size is 5 inches.
*Borne.*—Singly.
*Stems.*—Very long. Average length is about 18"–24".

*Form.*—When first open: High centered. With outer petals recurling backwards and retains its form to the end.

*Petalage.*—Length typically about 1.6"–1.8". Width typically about 1.4"–1.6". Margins — entire. Number of petals under normal conditions: 26–32.

*Color.*—When first opened, the upper side is close to Yellow-Orange Group 19-D tinged Red Purple Group 60-A at the edge. The underside is tinged Red Group 47-A, blending to Yellow-Orange Group 15-B at the center.

*Color change.*—When the flower is fully open, the upper side of the outer petals is Red Purple Group 74-A on the edge, blending to Red Group 56-C near the middle to Yellow Group 13-B near the center. The inner petals are close to Yellow Group 13-B tinged with Red Purple Group 74-C toward the edge. The color holds from 7 to 10 days when cut.

*Fragrance.*—Moderate rose fragrance.

C. Petals:

*Texture.*—Thick with smooth upper surface and satin reverse.

*Shape.*—Oval with pointed tip.

*Form.*—Tips recurl with moderate quilling.

*Arrangement.*—Symmetrically arranged in a circular outline. Imbricated, with few petaloids in the center.

*Persistence.*—Drop off cleanly.

*Lasting quality.*—On the plant: Long, 7–10 days. As a cut flower: Longer, 9–12 days.

REPRODUCTIVE PARTS

A. Reproductive parts:

*Stamens.*—Length — about ¼ to ½ inch.

*Anthers.*—Size: Medium, about ⅛ inch. Quantity: Many, about 40–46. Color: Yellow-Orange, near Yellow-Orange Group 22-A. Arrangement: Regular around styles.

*Filaments.*—Color: Yellow-Orange, near Yellow-Orange Group 16-A.

*Pollen.*—Color: Lemon Yellow, near Yellow Group 8-B.

*Styles.*—Color: Red, near Red Group 46-B.

*Stigmas.*—Color: Yellow-Orange Group 14-C.

*Pistils.*—Many, about 80 to 100; Length — about 1/16 to ⅛ inch.

B. Hips:

*Shape.*—Globular.

*Size.*—Medium. Length — ½ to ¾ inch.

*Color.*—Orange Group 28-B.

*Do seeds protrude.*—Slightly.

C. Seeds: Firm with tannish-brown coating. Irregularly shaped. Few in pod.

PLANT

A. Form: Upright.

B. Growth: Very vigorous, uniform branching on main stems, new growth occurs regularly throughout season. Height obtained in first season — 3½ to 4 ft. Mature Plant: Tall: 4½ to 5 ft. Width — 2½ to 3½ ft.

C. Foliage: Compounded 3 to 5 leaflets on single bloom, 5 to 7 leaflets on main canes.

*Size.*—Medium to large. Leaflets — 2½ to 3¾ inches long and 1½ to 2½ inches wide.

*Quantity.*—Abundant, covers plant to ground.

*Arrangement.*—Alternate; Uniform and equally spaced.

*Color.*—New foliage: Upper side — near to Green Group 137-A with leather glossy foliage; under side — dull, near Green Group 147-C. Old foliage: upper side — Green Group 135-A, under side — Green Group 147-B.

*Shape.*—Oval with slight point at tip.

*Venation.*—Parallel.

*Texture.*—Upper side — leathery, glossy. Under side — smooth between ribs.

*Edge.*—Serrated.

*Serration.*—Very small and uniform.

*Petiole.*—Color: Upper side — Green Group 137-B. Under side — Green Group 137-C. Texture — Smooth. Length — 2½ to 4 inches.

*Rachis.*—Color — Green Group 137-B. Texture — Smooth.

*Stipules.*—Shape — Narrow and pointed. Texture — Medium smooth. Color — Green Group 137-A. Length — ½ to 1 inch.

*Resistance to disease.*—Blackspot — highly resistant. Mildew — highly resistant. Rust — not observed.

D. Wood:

*New wood.*—Color — Green Group 138-C. Bark — smooth.

*Old wood.*—Color — Green Group 139-B. Bark — smooth.

E. Thorns:

*Thorns.*—Quantity — ordinary. On laterals from stalk — few. Form — flat base. Length — about ¼ to ½ inch. Color (when young) — Green Group 148-C. Position — irregular.

*Prickles.*—Quantity — few. On laterals — very few. Size — about ⅛ inch. Shape — curved down. Color (when young) — amber green. Color (when mature ) — brown with mahogany coat.

F. Winter hardiness: Excellent. Hardy to zone 4.

I claim:

1. A new and distinct variety of rose plant of the hybrid tea class, substantially as herein shown and described, characterized particularly as to novelty by the unique combination of its exceptionally strong stems; its long, bright purple red and yellow buds; its large, bright purple red flowers with deep yellow reverse; and its vigorous, upright habit of growth.

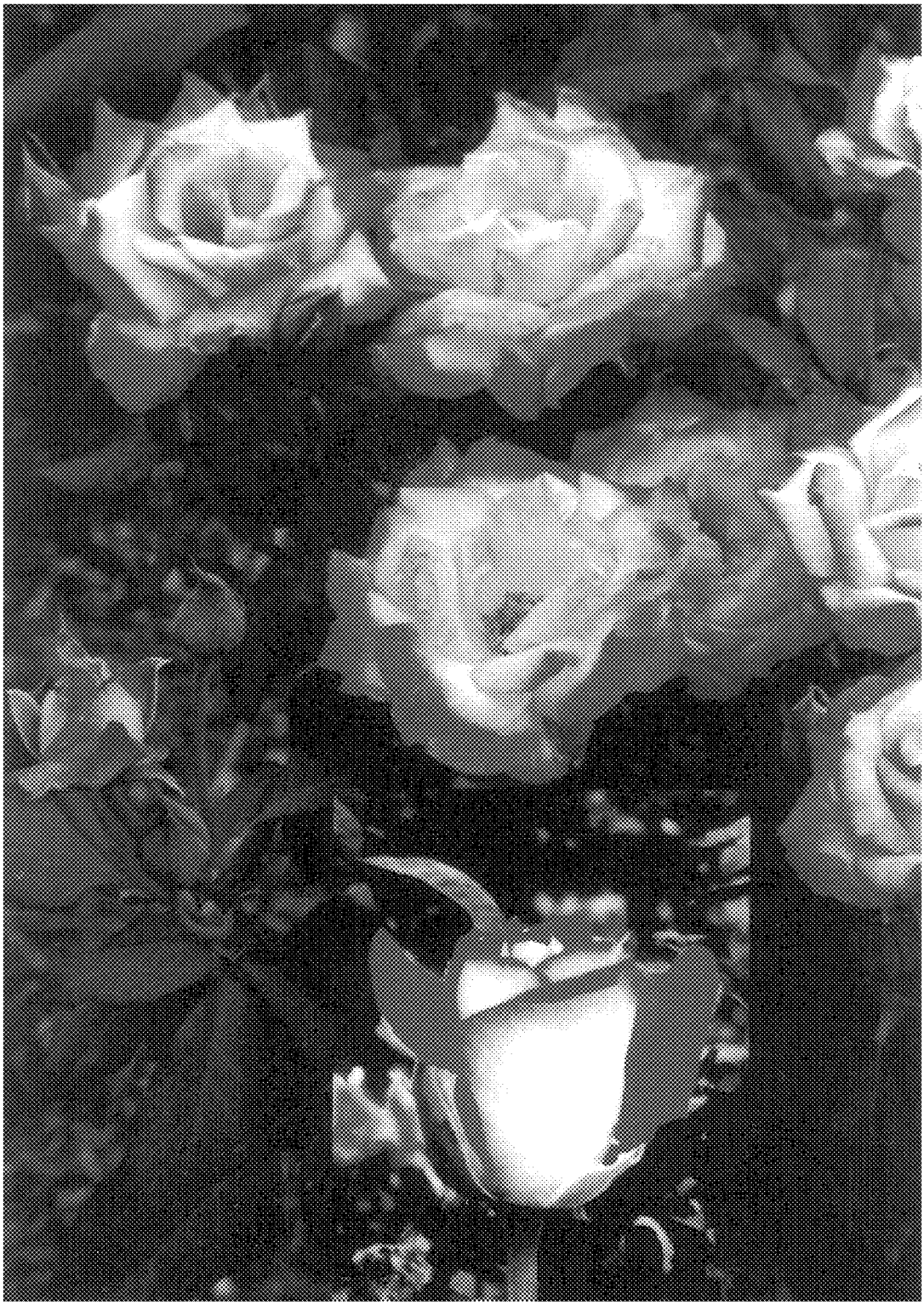

* * * * *